United States Patent
Walter et al.

(10) Patent No.: US 6,419,959 B1
(45) Date of Patent: Jul. 16, 2002

(54) GALENIC COMPOSITION CONTAINING OPIOID ANTAGONISTS

(75) Inventors: Kersten Walter; Thomas Profitlich, both of Munich (DE)

(73) Assignee: Klinge Pharma GmbH, Munich (DE)

( * ) Notice: Subject to any disclaimer, the term of this patent is extended or adjusted under 35 U.S.C. 154(b) by 0 days.

(21) Appl. No.: 09/319,818

(22) PCT Filed: Dec. 4, 1997

(86) PCT No.: PCT/EP97/06789

§ 371 (c)(1),
(2), (4) Date: Aug. 10, 1999

(87) PCT Pub. No.: WO98/25613

PCT Pub. Date: Jun. 18, 1998

(30) Foreign Application Priority Data

Dec. 11, 1996 (DE) .......................................... 196 51 551

(51) Int. Cl.⁷ .......................... A61K 31/44; A61K 9/16; A61K 9/14; A61K 9/20; A61K 9/28
(52) U.S. Cl. ....................... 424/490; 424/489; 424/464; 424/474; 424/458; 424/468; 514/282
(58) Field of Search ................................ 424/458, 464, 424/468, 489, 490, 474; 514/282

(56) References Cited

U.S. PATENT DOCUMENTS

| 3,966,940 A |   | 6/1976 | Pachter et al. ............... 424/260 |
| 4,774,230 A |   | 9/1988 | Tuttle et al. .................... 514/27 |
| 4,987,136 A | * | 1/1991 | Kreek et al. ................. 514/282 |

FOREIGN PATENT DOCUMENTS

| DE | 43 25 465 | 2/1995 |
| EP | 0 352 361 | 1/1990 |
| WO | WO 83/03197 | 9/1983 |
| WO | WO 97/33566 | 9/1997 |

OTHER PUBLICATIONS

Remingtons Pharmaceutical Sciences, 18th edition, pp. 1669–1670.*
M. Dittgen et al., "Acrylic polymers A review of pharmaceutical applcations", *STP Pharma Sciences*, 7(6), 403–437 (1997); especially Table II on p. 404.

R. Saller et al., *Schmerzen—Therapie in Praxis und Klinik*, Marseille Verlag, Munich, 1991, pp. 92–93.

L. Manara et al., "The Central and Peripheral Influences of Opioids on Gastrointestinal Propulsion", *Ann. Rev. Pharmacol. Toxicol.*, 25, 249–273 (1985).

J.C. Cameron, "Constipation related to narcotic therapy . . ."; *Cancer Nursing*, 15(5), 372–277 (1992).

P. Glare et al., "Unrecognized Constipation in Patients with Advanced Cancer . . .", *J. Pain Symptom Mgmt.*, 7, 369–371 (1992).

K.–O. Vollmer, "Pharmakokinetische Grundlagen des Valaron–N–Prinzips", *Fortschr. Med.*, 106, 593–596 (1988).

G. Basilisco et al., "effect of loperamide and naloxone on mouth–to–caecum transit time . . . ", *Gut*, 26, 700–703 (1985).

G. Basilisco et al., "Oral Naloxone Antagonizes Loperamide–Induced Delay of Orocecal Transit", *Dig. Dis. Sci.*, 32(8), 829–832 (1987).

J.A. Culpepper–Morgan et al., "Treatment of opioid–induced constipation . . . ", *Clin. Pharmacol. Ther.*, 52, 90–95 (1992).

N.P. Sykes, "Oral naloxone in opioid–induced constipation", *Lancet*, 337, 1475 (1991).

B.A. Robinson et al., "Oral naloxone in opioid–induced constipation", *Lancet*, 338, 581–582 (1991).

* cited by examiner

Primary Examiner—Thurman K. Page
Assistant Examiner—Amy E Pulliam
(74) Attorney, Agent, or Firm—Heller Ehrman White & McAuliffe LLP

(57) ABSTRACT

A pharmaceutical composition for oral administration contains naloxone-, N-methylnaloxone- and/or N-methylnaltrexone-containing particles which release the active substance depending on the ambient pH. This ensures the liberation of the active substance over the whole gastrointestinal tract. The side effects caused by the use of analgesic opioids, such as constipation, are thus eliminated without reducing the analgesic effect.

17 Claims, No Drawings

GALENIC COMPOSITION CONTAINING OPIOID ANTAGONISTS

The invention relates to new galenic compositions with opioid antagonistic activity and their use in opioid-induced constipation. In particular, the invention relates to pellet, granulate or microtablet compositions comprising the active ingredients naloxone, N-methylnalaxone or N-methylnaltrexone as the active ingredients with opioid antagonistic activity.

Constipation arising through medication with the use of strongly effective analgesics of the morphine type represents a large problem. It is considered as one of the most frequent side effects and is an undesired concomitant symptom particularly in continual therapy. This problem arises during treatment in approximately 85% of the patients given morphine. In contrast to other side effects caused by for example morphine, this is a chronic phenomenom that does not loose intensity during the course of treatment [Saller R., Hellenbrecht D. "Schmerzen-Therapie in Praxis und Klinik", 1st Ed. (1991) Marseille Publishers, Munich]. The paralytic effect of opioids on intestine motility has been known for a long time and is also therapeutically used, for example, in the case of diarrheal illnesses [Manara L., Bianchetti A. "The central and peripheral influences of opioids on gastrointestinal propulsion", Ann. Rev. Pharmacol. Toxicol. 25, 249–273 (1985)]. Although the mode of action of opioids on intestine motility is not yet completely understood, it is seen in connection with the binding of the opioid to opioid receptors in the intestine. Aside from in the brain, these opioid receptors are also to be found at high density in the gastrointestinal tract above all [Manara L., Bianchetti A. "The central and peripheral influences of opioids on gastrointestinal propulsion", Ann. Rev. Pharmacol. Toxicol. 25, 249–273 (1985)].

In a series of pharmacological experiments, it could be demonstrated that opioids (morphine was mostly chosen as a model substance) have a direct effect on the smooth musculature of the intestine and, thus, muscle tonicity in intestine segments increases. The enhancement of segmental tonicity leads to a significant prolongation of gastrointestinal passage time with simultaneous decrease of the propulsive motility of the intestine [Cameron J. C. "Constipation related to narcotic therapy", Cancer Nurs. 15, 372–377 (1992)].

The aim of a therapy is to neutralize this peripheral side effect of morphine and related compounds because opioid-induced constipation can be very painful and finally endangers the success of treatment [Glare P., Lickiss J. N. M. "Unrecognized constipation in patients with advanced cancer: a recipe for therapeutic disaster", J. Pain Symptom Manage. 7, 369–371 (1992)]. A little more than half of the patients who suffer from this side effect can be sufficiently taken care of with customary laxatives and thickening agents. For the rest of the patients, satisfactory treatment possibilities are still lacking.

Since it is assumed in opiod-induced constipation that the true effect proceeds directly and locally over the entire intestine through the occupation of opioid receptors, this effect should be able to be neutralized through the use of opioid antagonists. However, the use of opioid antagonists only makes sense when the antagonistic effect on the intestine is limited and the central pain-relieving effect is not neutralized. Therefore, only a few opioid antagonists such as for example naloxone, N-methylnalaxone or N-methylnaltrexone are considered which have a peripheral effect and not an effect in the CNS under certain conditions.

Naloxone is a pure opioid antagonist which is customarily intravenously applied as an antidote in the case of opioid poisoning. After oral administration, naloxone is quickly and completely resorbed. Since the substance is subject to a very pronounced first-pass metabolism, only small amounts of the unaltered substance are systemically available. The predominant portion of the applied substance is present in the blood in the form of the metabolites naloxone-3-glucuronide, β-naloxol-3-glucuronide and β-naloxol which are not effective or only weakly effective [Vollmer K. O. "Pharmakokinetische Grundlagen des Valoron-N-Prinzips", Fortsch. Med. 106, 593–596 (1988)]. As a result of this pharmakinetic property, naloxone in a suitable dose is an ideal candidate for relief of opioid-induced constipation: in the intestine, it is present as an active substance and can thus neutralize the paralytic effect of the opioid on the gastrointestinal tract and, after reabsorption, it is largely metabolized and rendered ineffective with the first liver passage. Thus, the pain-relieving effect of the opioids is not adversely affected.

In various small clinical trials, it could be demonstrated that opioid constipation could be partially neutralized by the oral administration of naloxone: in two studies on healthy probands, Basilisco et al. examined the influence of loperamide, a peripherally effective opioid used in diarrheal illnesses, on the gastrointestinal passage time. They demonstrated that naloxone when intravenously applied (40 μg/kg/hr. in 3 hr) [Basilisco G., Bozzani A., Camboni G., Recchia M., Quatrini M., Conte D., Penagini R., Bianchi P. A. "Effect of loperamide and naloxone on mouth-to-caecum transit time evaluated by lactulose hydrogen breath test", Gut 26, 700–703 (1985)] and after oral administration of relatively high doses of 16 or 32 mg [Basilisco G., Camboni G., Bozzani A., Paravicini M., Bianchi P. A. "Oral naloxone antagonizes loperamide-induced delay of orocecal transit", Dig. Dis. Sci. 32, 829–832 (1987)] could neutralize the constipating effect of loperamide.

Culpepper-Morgan et al. report a pilot study in which three patients with opioid-induced constipation were treated with orally applied naloxone. After doses of up to 16 mg, two of the three patients responded to the treatment (neutralisation of constipation). With the other patient, constipation could not be neutralized even with a increase in dose of up to 24 mg naloxone (within 3 hours). Plasma level determinations showed that dose-dependent maximal naloxone concentrations up to 7.9 ng/ml were measured. At doses from 14 mg, the non-responder showed clear withdrawal symptoms which points to an antagonization of the central opioid effect [Culpepper-Morgan J. A., Inturrisci C. E., Portenoy R. K., Foley K., Houde R. W., Marsh F., Kreek M. J. "Treatment of opioid-induced constipation with oral naxolone: A pilot study", Clin. Pharmacol. Ther. 52, 90–95 (1992)].

Sykes report a study with 12 patients who were administered with oral naloxone at different doses. The naloxone dose was oriented on the daily opioid dose. Naloxone was given in doses of 0.5%, 1%, 2%, 5%, 10%, 20%, and 40% with respect to the opioid dose. No effect was determinable up to 10% naloxone dose. A neutralization of constipation was first reported at the very high dose range (20% to 40%) The absolute naloxone doses which were administered could amount to up to 72 mg naloxone [Sykes N. P. "Oral naloxone in opioid-associated constipation", The Lancet 337, 1475 (1991)].

Robinson et al. report a study on 12 patients with opioid-induced constipation in which naloxone was also orally administered. The maximally administered dose was 12 mg naloxone. An effect on the gastrointestinal motility or withdrawal symptoms was not determinable in any of the treated patients [Robinson B. A., Johansson L., Shaw J. "Oral naloxone in opioid-associated constipation", The Lancet 338, 581–582 (1991)].

It is striking that in the cited studies, the results turn out very differently and, above all, naloxone is effective when it is applied in high doses. In this dose range, withdrawal symptoms also already arise in individual patients. The active ingredient is released quickly and unmodified in customary, simple compositions (for example, capsules or drops). When using these simple compositions, naloxone is quickly and completely resorbed in the upper part of the gastrointestinal tract. Undesired side effects can arise through the resulting, relatively high blood concentrations. Therapeutical applications of naloxone compositions of this type are described in EP 0 103 636 (A1) and EP 0 352 361 (A1) for example.

However, since the paralysis concerns the entire gastrointestinal tract and not only the duodenum and upper part of the small intestine, the problem of opioid-induced constipation cannot be solved with a composition of this type (for example drops).

DE 4325465 (A1) proposes a combination preparation of an opioid and an opioid antagonist for oral administration, wherein the opioid is released in a retarded manner and, in contrast, the opioid antagonist is quickly released, i.e. with low or no retardation. With respect to the portion of naloxone, this preparation corresponds to a non-modified, quick-releasing composition with the above mentioned disadvantages. Namely, this path increases the danger of an undesired systemic naloxone effect whereby the pain-relieving effect of the opioid is neutralized again. Therefore, using the teaching of DE 4325465 (A1), a complete elimination of these side effects cannot be attained and/or withdrawal symptoms can further occur in patients at the chosen dose ranges.

Correspondingly, the invention has the object of providing an oral, galenic composition with opioid antagonistic activity that, as a result of pharmaceutical-technological properties, is capable of neutralizing opioid-induced constipation without leading thereby to significant systemic availability of naloxone and thus antagonizing the opioid effect in the CNS.

The invention is based on the recognition that an effective antagonization of the opioid effect on the upper and lower parts of the gastrointestinal tract with avoidance of the systemic antagonization of the opioid effect can only then take place when the active ingredient is released in a modified manner over the entire digestive tract. In this connection, the control of the release occurs site-specifically over the various ambient pHs in the respective stomach and/or intestine sections whereby this does not concern a retardation in the sense of a delayed release. Here, when constipation is already present, the danger exists that the intestine passage of the composition is delayed and the active ingredient is prematurely released into the upper sections of the digestive tract whereas the lower sections are not given medical aid.

The above problem is solved by an orally administrable pharmaceutical composition comprising naloxone, N-methylnalaxone and/or N-methylnaltrexone, or a pharmaceutically acceptable salt thereof, as an active ingredient, wherein the release of the active ingredient is achieved over the entire digestive tract by particles contained in the composition which release the active ingredient initially and as a function of the ambient pH. The following embodiments on naloxone apply in the same manner for N-methylnalaxone, N-methylnaltrexone, pharmaceutically acceptable salts of these compounds and mixtures thereof.

Preferred embodiments of the invention are given in the dependent claims.

The naloxone composition according to the invention is distinguished by a targeted and controlled release of active ingredient as uniformly as possible over the entire gastrointestinal tract, i.e. from stomach to colon, wherein a quick release of active ingredient occurs locally in the individual sections of the digestive tract. Since, in contrast to time-dependent, controlled releasing systems, the release of active ingredient is not controlled by the delayed release, but instead, over the varying pH conditions in the digestive tract, the opioid-induced constipation and the delayed gastrointestinal transit of the active ingredient carrier associated therewith (pellets or others) does not lead to an uncontrolled release of the medicament in intestine sections in which it should not be released. Hereby, the composition according to the invention results in the advantage that a smaller single dose can be employed.

In a preferred embodiment, the particles containing active ingredient are provided with a coating that is soluble as a function of the ambient pH. For a coating of this type, customary film-forming substances with a solubility differing as a function of ambient pH can be used. The acryl polymers of the Eudragit® series known and used in galenics, especially Eudragit®L100–55, Eudragit®L-100 and Eudragit®S100 (obtainable from Röhm Pharma GmbH, Weiterstadt, Germany) are preferred. The desired release pH can be adjusted in a targeted manner by suitable mixing of these substances and/or the active ingredient particles coated with these substances.

The possible decrease of the systemic load and the applied dose via the principle of "drug targeting" is a further advantage. As a mono-preparation, the medicament according to the invention additionally allows the use of the most varied opioids for constipation, however, it can also be employed as a combination preparation with a certain opioids, especially morphin, or one or more substances of the morphine type. A selection of such opioids comprises for example codeine, dihydrocodeine, hydromorphone, levomethadone, oxycodone, pethidine and propoxyphene and/or salts thereof. The dosage of the opioid depends on age, sex and the seriousness of the illness of the patients and can be adjusted by the attending physician based on his expert knowledge.

Preferred pharmaceutical medicaments contain naloxone-containing particles (pellets, microtablets or granules) with different lacquer coatings. The particles should preferably be designed such that they pass the pylorus substantially independent of the motility of the digestive tract. For this, a maximal size of approximately 2 mm is favorable. Typically, the pellets have a diameter of approximately 1 mm; the describe microtablets one of approximately 2 mm. The average particle size of the granulate is smaller than approximately 1 mm, preferably approximately 300 to approximately 600 $\mu$m. The lacquers on the particles differ by their different solubility characteristics. The solubility of the lacquers and the release of the medicament associated therewith depend on the local pH value of the digestive tract. A mixture of different particles with different release behaviours takes advantage of the strongly varying pH conditions in the digestive tract (stomach approximate pH 1.2, colon approximate pH 7.0).

Preferably, the pharmaceutical composition according to the invention contains at least two types of particles which each release the active ingredient at a different ambient pH. Since opioid-induced constipation in humans occurs to approximately 50% as a result of a delayed gastric emptying and to 25% through the weakened propulsive peristalsis in the small and large intestine regions respectively[Manara L., Bianchetti A. "The central and peripheral influence of opioids on gastrointestinal propulsion", Ann. Rev. Pharmacol. Toxicol. 25, 249–273 (1985)], an initial release of a certain amount of active ingredient is recommended as soon as the composition arrives in the stomach. For this purpose, the first type of particles can be designed such that the active ingredient is already released at the ambient pH of the stomach. The second particle type then releases the active ingredient at the ambient pH of the lower intestinal tract, i.e. a pH of approximately 7.0. In practice, the first type of particles can already release the active ingredient in a pH independent manner upon contact with an aequeous medium. This initial release can be achieved by providing the first type of particles with a coating comprising methylhydroxypropyl cellulose, and optionally polyethylene glycol (for example Macrogol® 6000; average molecular weight 6000), as an adjuvant which is soluble in aqueous medium independent of the pH value.

In a preferred embodiment, the ratio of the particles of the first type to the particles of the second type is 1:10 to 10:1, more preferably approximately 1:1. Additionally, further types of particles can be present which release the active ingredient by an ambient pH of approximately 5.5 to 6.5.

In a further preferred embodiment, the pharmaceutical composition comprises a first type of particles which release the active ingredient upon contact with an aqueous medium in a pH independent manner and a second or more types of particles which release the active ingredient at an ambient pH of approximately 5.5 to 7.0.

Thus, in the finished medicament (for example, hard gelatine capsules) a mixture of laminated particles is present which releases the active ingredient in a controlled and modified manner in the stomach, upper and lower small intestine and in the colon. The composition according to the invention can be administered in order to treat an opioid-induced constipation which already exists. However, it can also be given precautionarily in order to prevent from the outset the occurence of constipation with an opioid analgesic treatment.

EXAMPLES

The following non-limiting examples provide preferred embodiments of the invention.
Formulation Examples for Naloxone Pellets

Example 1

Naloxone Pellets Type A (pH Independent Release in the Upper Gastrointestinal (GI) Tract)

| core | |
|---|---|
| naloxone HCl | 2.00 mg |
| saccharose | 42.00 mg |
| corn starch | 12.50 mg |
| polyvidone | 3.50 mg |
| film coating | |
| methylhydroxypropyl cellulose | 1.80 mg |
| Macrogol 6000 | 0.18 mg |
| talcum | 2.02 mg |
| | 64.00 mg |

Example 2

Naloxone Pellets Type B (Release in Intestine Sections with a pH Milieu of Approximately 5.5)

| core | |
|---|---|
| naloxone HCl | 2.00 mg |
| saccharose | 42.00 mg |
| corn starch | 12.50 mg |
| polyvidone | 3.50 mg |
| film coating | |
| Eudragit ® L 100-55 | 12.00 mg |
| triethyl citrate | 1.20 mg |
| talcum | 3.80 mg |
| | 77.00 mg |

Example 3

Naloxone Pellets Type C (Release in Intestine Sections with a pH Milieu of Approximately 6.0)

| core | |
|---|---|
| naloxone HCl | 2.00 mg |
| saccharose | 42.00 mg |
| corn starch | 12.50 mg |
| polyvidone | 3.50 mg |
| film coating | |
| Eudragit ® L 100 | 12.00 mg |
| triethyl citrate | 1.20 mg |
| talcum | 3.80 mg |
| | 77.00 mg |

Example 4

Naloxone Pellets Type D (Release in Intestine Sections with a pH Milieu of Approximately 6.5)

| core | |
|---|---|
| naloxone HCl | 2.00 mg |
| saccharose | 42.00 mg |
| corn starch | 12.50 mg |
| polyvidone | 3.50 mg |
| film coating | |
| Eudragit ® L 100 | 6.00 mg |
| Eudragit ® S 100 | 6.00 mg |
| triethyl citrate | 1.20 mg |
| talcum | 3.80 mg |
| | 77.00 mg |

Example 5

Naloxone Pellets Type E (Release in Intestine Sections with a pH Milieu of Approximately 7.0)

| core | |
|---|---|
| naloxone HCl | 2.00 mg |
| saccharose | 42.00 mg |
| corn starch | 12.50 mg |
| polyvidone | 3.50 mg |
| film coating | |
| Eudragit ® S 100 | 12.00 mg |
| triethyl citrate | 1.20 mg |
| talcum | 3.80 mg |
| | 77.00 mg |

In Examples 1 to 5, the pellet cores are produced according a known method (for example extruding and subsequent rounding, adsorption of the active ingredient to the starter cores in the fluid-bed) and subsequently laminated. Filling of the pellets occurs in hard-gelatine capsules.

The simplest pellet combination contains the pellet types A and E in a ratio of 1:10 and/or 10:1, but preferably 1:1.

The pellet types B, C and/or D can be mixed into the above-mentioned mixture so that the medicament is uniformly distributed in the gastrointestinal tract. The total dose of naloxone HCl in a capsule can be between approximately 1 mg and approximately 30 mg, preferably approximately 1 mg and approximately 10 mg.

Formulation Examples for Microtablets

Example 6

Naloxone Microtablets Type A (pH Independent Release in the Upper GI-tract)

| core (diameter: 2 mm) | |
|---|---|
| naloxone HCl | 0.20–0.50 mg |
| lactose | 6.40–6.70 mg |
| microcrystalline cellulose | 2.00 mg |
| L-HPC | 1.00 mg |
| magnesium stearate | 0.10 mg |
| film coating | |
| methylhydroxypropyl cellulose | 0.18 mg |
| Macrogol 6000 | 0.018 mg |
| talcum | 0.202 mg |
| | 10.40 mg |

Example 7

Naloxone Microtablets Type B (Release in the Intestine Sections with a pH Milieu of Approximately 5.5)

| core (diameter: 2 mm) | |
|---|---|
| naloxone HCl | 0.20–0.50 mg |
| lactose | 6.40–6.70 mg |
| microcrystalline cellulose | 2.00 mg |
| L-HPC | 1.00 mg |
| magnesium stearate | 0.10 mg |
| film coating | |
| Eudragit ® L 100-55 | 0.80 mg |
| triethyl citrate | 0.08 mg |
| talcum | 0.12 mg |
| | 11.00 mg |

Example 8

Naloxone Microtablets Type C (Release in Intestine Sections with a pH Milieu of Approximately 6.0)

| core (diameter: 2 mm) | |
|---|---|
| naloxone HCl | 0.20–0.50 mg |
| lactose | 6.40–6.70 mg |
| microcrystalline cellulose | 2.00 mg |
| L-HPC | 1.00 mg |
| magnesium stearate | 0.10 mg |
| film coating | |
| Eudragit ® L 100 | 0.80 mg |
| triethyl citrate | 0.08 mg |
| talcum | 0.12 mg |
| | 11.00 mg |

Example 9

Naloxone Microtablets Type D (Release in Intestine Sections with a pH Milieu of Approximately 6.5)

| core (diameter: 2 mm) | |
|---|---|
| naloxone HCl | 0.20–0.50 mg |
| lactose | 6.40–6.70 mg |
| microcrystalline cellulose | 2.00 mg |
| L-HPC | 1.00 mg |
| magnesium stearate | 0.10 mg |
| film coating | |
| Eudragit ® L 100 | 0.40 mg |
| Eudragit ® S 100 | 0.40 mg |
| triethyl citrate | 0.08 mg |
| talcum | 0.12 mg |
| | 11.00 mg |

Example 10

Naloxone Microtablets Type E (Release in Intestine Sections with a pH Milieu of Approximately 7.0)

| core (diameter: 2 mm) | |
|---|---|
| naloxone HCl | 0.20–0.50 mg |
| lactose | 6.40–6.70 mg |
| microcrystalline cellulose | 2.00 mg |
| L-HPC | 1.00 mg |
| magnesium stearate | 0.10 mg |

-continued

| film coating | |
|---|---|
| Eudragit ® S 100 | 0.80 mg |
| triethyl citrate | 0.08 mg |
| talcum | 0.12 mg |
| | 11.00 mg |

For the Examples 6 to 10, the components of the tablet core (without magnesium stearate) are sieved and mixed in a suitable free-falling mixer for 15 min. After addition of the magnesium stearate, this is mixed for a further 10 min. The mass is subsequently pressed to microtablets on a tablet press with a special stamp (diameter 2 mm). The obtained microtablets are laminated in a suitable apparatus and filled into hard gelatine capsules.

The simplest combination of microtablets contains the types A and E in a ratio of 1:10 and/or 10:1, but preferably 1:1.

The pellet types B, C and/or D can be mixed into the above-mentioned mixture so that the medicament is uniformly distributed in the gastrointestinal tract. The total dose of naloxone HCl in a capsule can be between approximately 1 mg and approximately 30 mg, preferably approximately 1 mg and approximately 10 mg.

Formulation Examples for Granulates.

Example 11

Naloxone Granulate type A (pH Independent Release in Upper GI-tract)

| basis granulate | |
|---|---|
| naloxone HCl | 2.00–5.00 g |
| lactose | 65.00–68.00 g |
| microcrystalline cellulose | 20.00 g |
| L-HPC | 10.00 g |
| film coating | |
| methyhydroxypropyl cellulose | 2.70 g |
| Macrogol 6000 | 0.27 g |
| talcum | 3.03 g |
| | 106.00 g |

Example 12

Naloxone Granulate type B (Release in Intestinal Sections with a pH Milieu of Approximately 5.5)

| basis granulate | |
|---|---|
| naloxone HCl | 2.00–5.00 g |
| lactose | 65.00–68.00 g |
| microcrystalline cellulose | 20.00 g |
| L-HPC | 10.00 g |
| film coating | |
| Eudragit ® | 20.00 g |
| triethyl citrate | 2.00 g |
| talcum | 3.00 g |
| | 125.00 g |

Example 13

Naloxone Granulate type C (Release in Intestinal Sections with a pH Milieu of Approximately 6.0)

| Basis granulate | |
|---|---|
| naloxone HCl | 2.00–5.00 g |
| lactose | 65.00–68.00 g |
| microcrystalline cellulose | 20.00 g |
| L-HPC | 10.00 g |
| film coating | |
| Eudragit ® L 100 | 20.00 g |
| triethyl citrate | 2.00 g |
| talcum | 3.00 g |
| | 125.00 g |

Example 14

Naloxone Granulate type D (Release in Intestinal Sections with a pH Milieu of Approximately 6.5)

| Basis granulate | |
|---|---|
| naloxone HCl | 2.00–5.00 g |
| lactose | 65.00–68.00 g |
| microcrystalline cellulose | 20.00 g |
| L-HPC | 10.00 g |
| film coating | |
| Eudragit ® L 100 | 10.00 g |
| Eudragit ® S 100 | 10.00 g |
| triethyl citrate | 2.00 g |
| talcum | 3.00 g |
| | 125.00 g |

Example 15

Naloxone Granulate type E (Release in Intestinal Sections with a pH Milieu of Approximately 7.0)

| Basis granulate | |
|---|---|
| naloxone HCl | 2.00–5.00 g |
| lactose | 65.00–68.00 g |
| microcrystalline cellulose | 20.00 g |
| L-HPC | 10.00 g |
| film coating | |
| Eudragit ® S 100 | 20.00 g |
| triethyl citrate | 2.00 g |
| talcum | 3.00 g |
| | 125.00 g |

The components of the basis granulate according to the Examples 11 to 15 are sieved and moistened in a suitable mixture with granulation fluid and granulated. The granulate is subsequently dried in a fluid-bed and sieved such that a granulate is obtained with an average particle size of preferably 300 to 600 μm. The granulates are laminated in a suitable apparatus. The total dose of the active ingredient in a granulate composition can be between approximately 1 mg and approximately 30 mg, preferably approximately 1 mg and approximately 10 mg.

It is fundamentally possible to mix different granulates in a desired ratio with each other.

The laminated granulates can be further processed as follows:

Filling into hard-gelatine capsules

Pressing to tablets after mixing suitable tablet adjuvants (for example microcrystalline cellulose, magnesium stearate)

Filling into sachets after mixing further adjuvants (for example saccharose, Na dioctylsulfosuccinate, xanthan gum, flavouring agents).

What is claimed is:

1. An orally administrable pharmaceutical composition comprising particles comprising an opioid antagonist selected from naloxone, N-methylnaloxone, and N-methylnaltrexone, or a pharmaceutically acceptable salt thereof, as an active ingredient, in an amount sufficient for the treatment or prevention of opioid-induced constipation, the composition comprising at least two types of particles, a first type of particles releasing the active ingredient in a pH-independent manner on contact with an aqueous medium or releasing the active ingredient as a function of a different ambient pH around the particles, the pH being that found within the stomach or duodenum, and a second type of particles releasing the active ingredient as a function of a different ambient pH around the particles, the pH being that found within the lower intestine, such that the active ingredient is released over the entire intestine, where at least the second type of particles comprise a coating which is soluble as a function of the ambient pH and comprises one or more film-forming substances selected from methacrylic acid copolymers.

2. The composition of claim 1 where the particles have an average diameter not larger than 2 mm.

3. The composition of claim 1 where the first type of particles release the active ingredient in a pH-independent manner on contact with an aqueous medium.

4. The composition of claim 3 where the first type of particles comprises a coating containing hydroxypropylmethyl-cellulose and optionally containing polyethylene glycol.

5. The composition of claim 1 where the ratio of the first type of particles to the second type of particles is 1:10 to 10:1.

6. The composition of claim 5 where the ratio of the first type of particles to the second type of particles is approximately 1:1.

7. The composition of claim 1 where the composition comprises a first type of particles that release the active ingredient in a pH-independent manner on contact with an aqueous medium and a second type of particles that release the active ingredient at an ambient pH of approximately 5.5 to 7.0.

8. A tablet, capsule, or granulate composition comprising the composition of claim 1 and customary pharmaceutically acceptable adjuvants.

9. The composition of claim 8 in unit dose form.

10. The composition of claim 9 comprising from approximately 1 mg to approximately 30 mg active ingredient.

11. The composition of claim 9 comprising from approximately 1 mg to approximately 10 mg active ingredient.

12. The composition of claim 1 further comprising an opioid selected from the group consisting of morphine, codeine, dihydrocodeine, hydromorphone, levomethadone, oxycodone, pethidine, and propoxyphene.

13. A method for the treatment or prevention of opioid-induced constipation comprising administering the composition of claim 1.

14. The method of claim 13 comprising the treatment of constipation caused by an opioid selected from the group consisting of morphine, codeine, dihydrocodeine, hydromorphone, levomethadone, oxycodone, pethidine, and propoxyphene.

15. The composition of claim 7 where the composition comprises a first type of particles that release the active ingredient in a pH-independent manner on contact with an aqueous medium and a second type of particles that release the active ingredient at an ambient pH of approximately 7.0.

16. The composition of claim 15 where the composition comprises a first type of particles that release the active ingredient in a pH-independent manner on contact with an aqueous medium, a second type of particles that release the active ingredient at an ambient pH of approximately 7.0, and at least a third type of particles that release the active ingredient at an ambient pH between approximately 5.5 to 6.5.

17. The composition of claim 1 comprising at least three types of particles, each type of particles releasing the active ingredient as a function of a different ambient pH around the particles.

* * * * *